United States Patent [19]
Carr

[11] Patent Number: 4,815,479
[45] Date of Patent: Mar. 28, 1989

[54] HYPERTHERMIA TREATMENT METHOD AND APPARATUS
[75] Inventor: Kenneth L. Carr, Harvard, Mass.
[73] Assignee: M/A COM, Inc., Burlington, Mass.
[21] Appl. No.: 896,020
[22] Filed: Aug. 13, 1986
[51] Int. Cl.⁴ ............................................. A61N 5/02
[52] U.S. Cl. ................................. 128/804; 128/653; 128/736
[58] Field of Search ............... 128/804, 399, 653, 736; 374/122

[56] References Cited
U.S. PATENT DOCUMENTS

| | | | |
|---|---|---|---|
| 4,312,364 | 1/1982 | Convert et al. | 128/736 X |
| 4,346,716 | 8/1982 | Carr | 128/736 X |
| 4,397,313 | 8/1983 | Vaguine | 128/804 X |
| 4,589,424 | 5/1986 | Vaguine | 128/804 |

FOREIGN PATENT DOCUMENTS

| | | | |
|---|---|---|---|
| 0158690 | 10/1985 | European Pat. Off. | 374/122 |
| 3431314 | 3/1986 | Fed. Rep. of Germany | 128/804 |
| 2000335 | 1/1979 | United Kingdom | 128/736 |

Primary Examiner—Lee S. Cohen
Attorney, Agent, or Firm—Wolf, Greenfield & Sacks

[57] ABSTRACT

A system and associated method that combines microwave detection (radiometry) with microwave heating (hyperthermia) for the treatment of cancer with a microwave radiometric detector is operable during a receive mode of operation to establish signal path characteristics and a microwave transmitter is operable during a transmit mode of operation to carry out the hyperthermia treatment. There is provided an antenna array of a plurality antennae disposed over the tumor site. These antennae are coupled to separate signal channels. During the receive mode of operation the separate channel signals are combined for coupling to the microwave radiometric detector to enable adjustment of the phase of the separate antenna signals so as to maximize the signal detected at the microwave radiometric detector. Thereafter, during the transmit mode of operation the microwave transmitter couples signals to the signal channels to provide beam focusing of the microwave energy on to the tumor site.

12 Claims, 3 Drawing Sheets

4,815,479

HYPERTHERMIA TREATMENT METHOD AND APPARATUS

BACKGROUND OF THE INVENTION

The present invention relates in general to an apparatus for hyperthermia treatment of cancerous tissue or cancerous tumors, and the associated method of hyperthermia treatment thereof. More particularly, the present invention relates to an apparatus and associated method for non-invasive cancer tumor treatment employing an active radiometer phased array technique.

It is known that a cancerous tumor may be treated successfully by raising the temperature of the tumor, a treatment generally referred to as hyperthermia. In this connection it is known that certain tumors either shrink or disappear at a temperature of approximately 43° C. Based on this knowledge, one preferred method of hyperthermia tumor treatment provides for heating the tumor to that temperature by preferably heating only the tissue at the tumor site.

In more recent years hyperthermia has been accepted as a cancer treatment modality. However, it is generally restricted in use as in adjunctive procedure to radiation therapy for superficial lesions only. The primary reason for limitation to superficial use is related to the inability to focus energy at depth in human tissue. In this connection one of the objects of the present invention is to provide a hyperthermia treatment apparatus and associated method that provides for energy focusing at depths in human tissue.

In hyperthermia apparatus, there have generally been attempted two different techniques for carrying out treatment. The first and more common technique utilizes non-microwave invasive thermometry to determine the transmitter power required to heat the tumor tissue. In this technique they employ multiple antennae and use amplitude control. This technique does not achieve beam forming.

Other techniques, utilize a radiometer receiver in conjunction with a transmitter to merely monitor temperature but do not achieve focusing with a beam Examples of such techniques are found in British Patent 2,000,335 to Sterzer and U.S. Pat. No. 4,312,364 to Convert et al.

Accordingly, it is an object of the present invention to provide an improved hyperthermia treatment method and apparatus that achieves focusing of the microwave energy on the tumor so as to optimize the coupling of energy to the tumor for treatment thereof.

Another object of the present invention is to provide an improved system and associated method that combines microwave detection (radiometry) with microwave heating (hyperthermia) for the treatment of cancer.

SUMMARY OF THE INVENTION

To accomplish the foregoing and other objects, features and advantages of the present invention there is provided a system for the hyperthermia treatment of cancerous tumors. This system is one that combines microwave detection with microwave heating for treatment purposes. The radiometer senses the emissivity of the tumor (target) to determine the path length (phase) between the surface of the body and the tumor. An antenna array is provided which includes a plurality of antennae adapted to be disposed over the tumor site. The number of antennae is determined by the size and depth of the tumor which are known factors. During the receive mode of operation, means are provided for combining signals from the antennae to provided a combined signal including means for separately adjusting the phase of each of the antenna signals to maximize the signal detected at the radiometer. The radiometer is thus employed to achieve phase coherency. It is noted that the tumor itself in this technique functions as the signal generator thus permitting the tissue to become a known transmission path. Phase adjustment of the individual paths provides phase coherency to the tumor, taking in to account tissue layering, variations, and inhomogeneity. The system also includes a transmitter means and means for dividing the transmitter means signal for coupling to the antenna array. By reciprocity, the transmit path during the transmit mode of operation is phase coherent allowing uniform power coupling to the primary tumor site.

In accordance with the method of the present invention it is practiced in a system that comprises a microwave radiometric detector operable during a receive mode of operation to establish signal path characteristics and a microwave transmitter operable during a transmit mode of operation. The method of hyperthermia treatment for a cancerous tumor comprises the steps of providing an antenna array of a plurality of antennae disposed over the tumor site, providing separate bi-directional signal channels each coupled to one of the antennae of the antenna array, and combining the separate channel signals for coupling to the microwave radiometric detector during the receive mode of operation. The phase of the separate antenna signals is adjusted so as to maximize the signal detected at the microwave radiometric detector. This establishes the signal path characteristics. Next is the step of operating the microwave transmitter and dividing the microwave transmitter signal for coupling to the signal channels during the transmit mode of operation to provide beam focusing of the microwave energy on to the tumor site.

DESCRIPTION OF THE DRAWINGS

Numerous other objects, features and advantages of the invention should now be become apparent upon reading of the following detailed description taken in conjunction with the drawings, in which.

DETAILED DESCRIPTION

Figure 1:
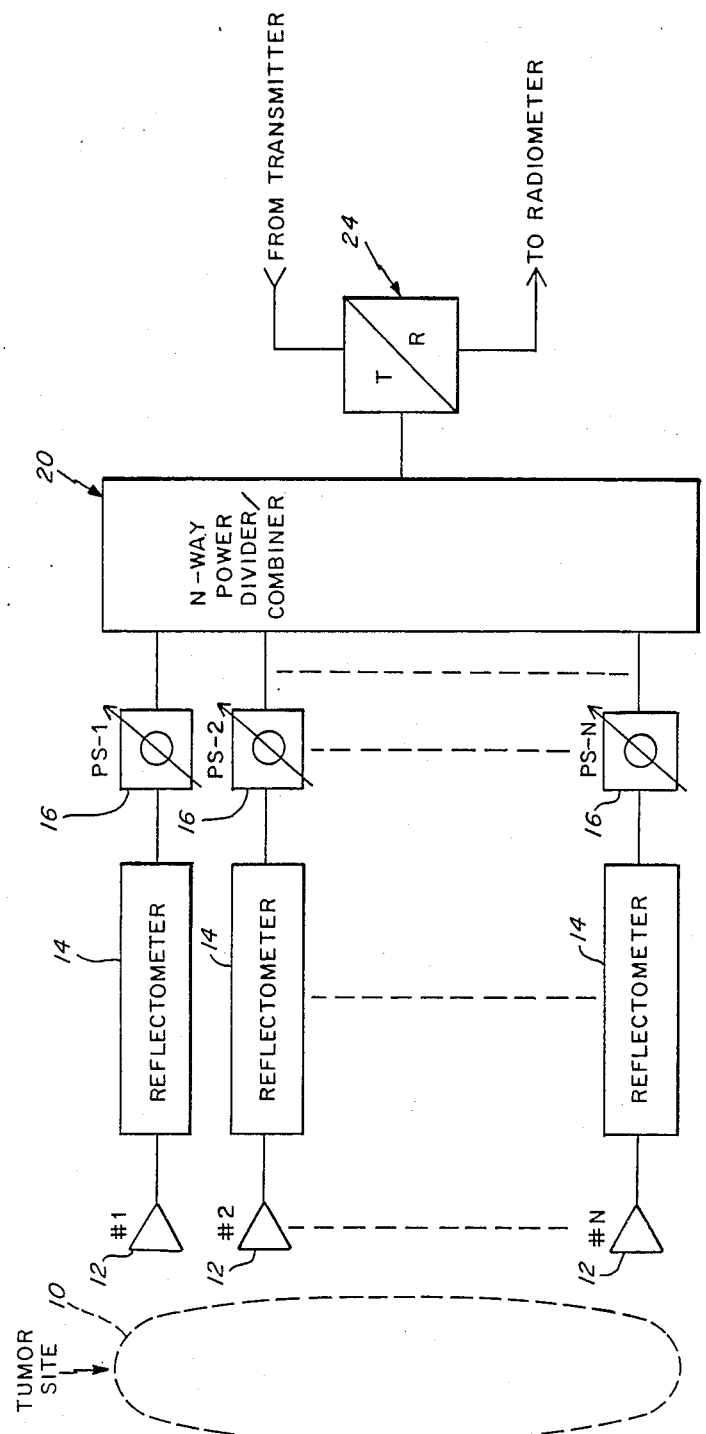
FIG. 1 is a block diagram of a one embodiment of the present invention.
Figure 2:
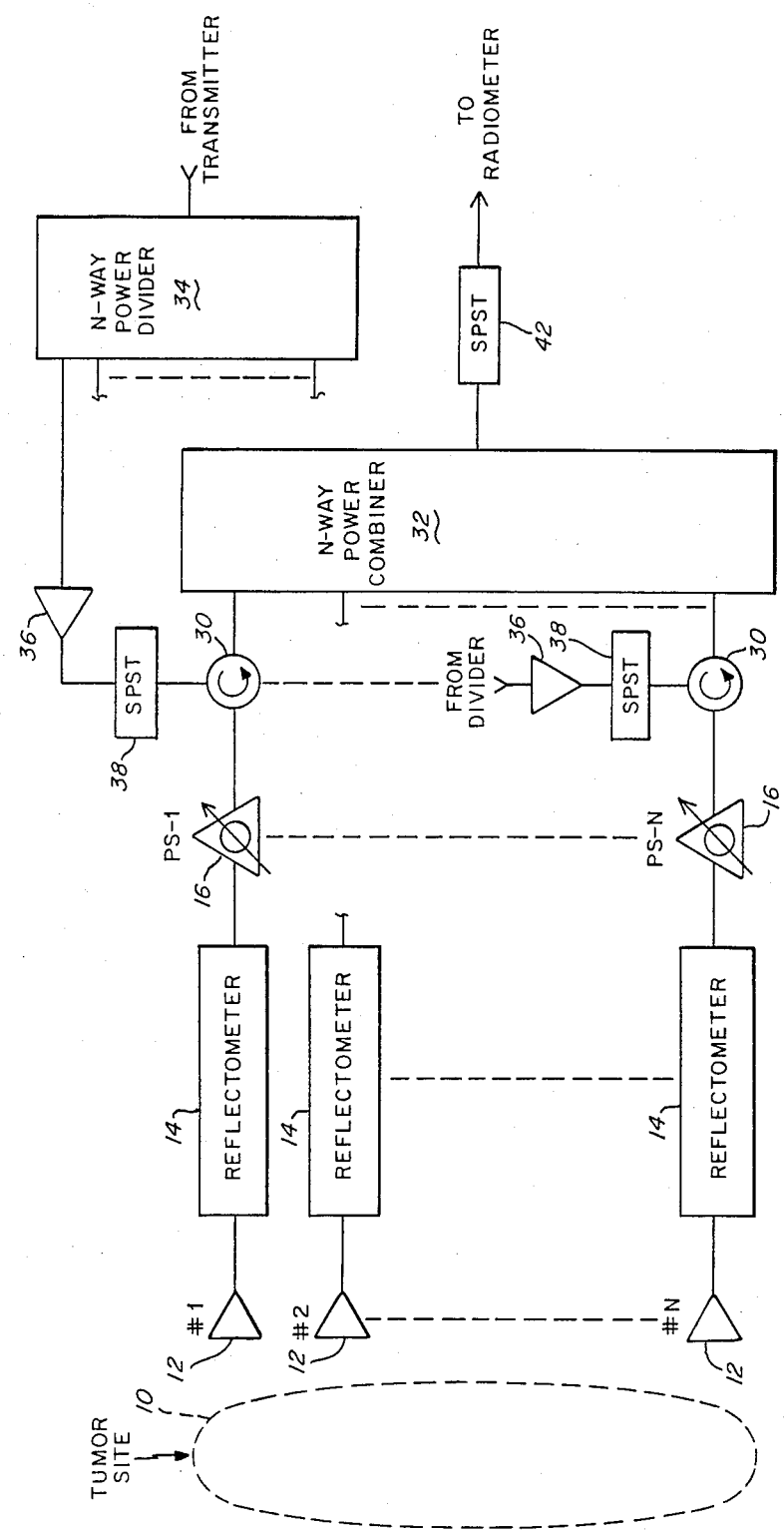
FIG. 2 is a block diagram of a second embodiment of the present invention.

In accordance with the present invention as illustrated by the embodiments of FIGS. 1 and 2 herein, there is provided a system and associated method for combining microwave detection (radiometry) with microwave heating (hyperthermia) for the treatment of cancer and in particular cancerous tumors. Unlike prior systems, the system of the present invention with the preferred use of the radiometer senses the emissivity of the tumor to determine the path length (phase) between the surface of the persons body and the tumor. In this connection the technique of the present invention assumes that one has located the tumor and now wishes to treat the tumor using microwave hyperthermia. Once the tumor location and mass are know such as by techniques described in my co-pending application Ser. No. 06/795,976 filed Nov. 7, 1985 pertaining to Method and Apparatus for Cancerous Tumor Detection, then a particular antenna array may selected for hyperthermia treatment. In the array the number of antennae employed is determined by the size and depth of the tumor. The use of multiple antennae distributes the heat at the body surface minimizing undesired surface heating.

In accordance with the invention a radiometer is employed to achieve phase coherency. The signal level at the output of the radiometer is optimized by adjusting the phase of each of the receiving paths.

In past hyperthermia systems phase coherency has only been obtained for a portion of the signal path. Phase coherency can only be obtained in the normal microwave equipment path. For example, phase coherency can only be controlled between the microwave transmitter, the source of heating, and the antenna element; the tissue path from the antenna element to the tumor site is unknown. However, in accordance with the present invention the signal path is made determinative by the concept of consideration of the tumor itself as a signal generator. A phase adjustment of the separate signal paths from the separate antennae during a receive mode of operation of the invention provides phase coherency when signals are subsequently coupled to the tumor during the transmit mode of operation. Thus, this phase adjustment of the separate signal paths or channels provides phase coherency to the tumor, taking in to account tissue layering variations and inhomogeneity.

The system of the present invention operates on the basis of reciprocity. This reciprocity concept means that once the phase adjustments occur during the receive mode of operation, when the tumor is functioning as a signal generator, these same settings of phase are subsequently used during the transmit mode of operation to provide phase coherency allowing uniform power coupling to the primary tumor site.

Phased-array transmission systems are known, such as are presently used in sophisticated radar designs. However, attempts to achieve beam forming through the use of such phased array technique has proven not to be successful due primarily to the fact that the human body, unlike free space is layered, non-homogeneous and lossy. In this regard, in free space, phase coherency is not a problem and can be easily achieved because free space is low loss, uniform or homogeneous and common to all elements of the array with respect to the target. In such systems only the phase coherency within the system, up to and including the antenna element, is of concern. Also, in an active radar, in a free space phased-array system, the target is illuminated by the transmit signal. The echo or reflection is in return received allowing determination of distance by measurement of time between the transmit and receive signals. Also, in such systems detection is accomplished at the same frequency as the transmit frequency. On the other hand in accordance with the present invention such techniques are not usable because of the aforementioned non-homogeneous and lossy nature of tissue.

In summary, in a non-homogeneous, layered and lossy media such as human tissue, phase coherency is extremely difficult if not impossible to achieve through the use of normal phased array techniques. It is only through the technique of the present invention that a proper additive beam can occur by virtue of dual mode operation including a receive mode in which the tumor itself functions as a signal generator with the associated use of a radiometer for adjusting phase to maximize signal detection. This is coupled with the transmit mode of operation in which the previously established phase settings are now employed, with the system incorporating a microwave transmitter for coupling signals along the same pre-established and preset paths thus providing proper beam forming and desired signal path characteristics. Again, the natural emissivity of the target (in this case, the tumor) determines the signal transmission characteristics. The receiver is preferably a radiometer capable of measurement of actual body emission. Radiometry is the measurement of received radiation. Radiometry is defined as the technique for measuring electromagnetic energy considered as from thermal radiation. Clinical radiometry, in turn, is the measurement of natural emission from the human body. In this connection any object above absolute zero radiates electromagnetic energy to an extent governed by its radiant emittance.

Reference is now made to FIG. 1 for an illustration of one embodiment of the present invention. In FIG. 1 the tumor site is illustrated generally at 10. The system illustrated in FIG. 1 is a multiple antennae system including a plurality of antennae 12 coupling by way of a plurality of reflectometers 14 and phase shifters 16 to the apparatus 20. The apparatus 20 is a combination power divider and combiner. On one side the apparatus 20 has a plurality of terminals coupling to the respective phase shifters 16. On the other side the apparatus 20 has a single terminal coupling to the switch 24. As illustrated in FIG. 1, the switch 24 in turn connects to the microwave transmitter on one side and to the detecting microwave radiometer on the other side.

As indicated previously, there are basically two separate modes of operation referred to herein as the receive mode of operation and the transmit mode of operation. These modes of operation are in essence mutually exclusive of each other. The signal path is defined during the receive mode of operation during which the phase shiftless are adjusted and thereafter the hyperthermia treatment actually occurs during the transmit mode of operation. The switch 24 is operated so as to control between these two different modes of operation. Likewise, an input may be provided to the apparatus 20 so that it functions as to be defined hereinafter, differently during transmit and receive modes of operation.

In the embodiment of FIG. 1 phase adjustment is carried out with the phase shifters 16 also identified as phase shifters PS1–PSN. The phase adjustment may be carried out either mechanically or electronically to allow maximizing of signal strength at the output of apparatus 20 coupled to the transmit/receive switch 24. This operation occurs during the receive mode of operation in which the apparatus 20 functions as an N-way combiner essentially combining all of the signals from the separate phase shifters to provide a single output signal coupled to the transmit/receive switch 24.

This adjustment of the phase shifters 16 basically adjusts the electrical length of each signal path from the tumor through the microwave path to the apparatus 20 functioning as an N-way power combiner to thus provide a phase additive situation. By reciprocity if one now disconnects the receiver (radiometer) and connects the transmitter one can now couple energy to the tumor in a like manner using the same signal paths and achieve a focused pattern. In this instance switch 24 is operative so that it is now in the transmit mode essentially disconnecting the radiometer and instead connecting the transmitter so that the transmitter is coupled by way of switch 24 to the apparatus 20. In the transmit mode of operation the apparatus 20 functions as an N-way power divider taking the signal input from the switch 24 and dividing it to the separate signal channels including separate phase shifters 16. These signals are then coupled by the previously set phase shifters to the antennae 12 for coupling signals to the tumor site 10.

During the transmit mode of operation, should the electrical path length change, due to the application of the hyperthermia heat, for example, the transmitter may be turned off and the radiometer may again be used to determine path length thereby continuously repeating the process and thus continuously monitoring the operation so that proper phase coherency is maintained. Again, this change from transmit to receive mode and back to transmit mode is controlled by the switch 24. This may be a manually operated switch.

In the closed loop system of FIG. 1, the radiometer may be used to monitor differential temperature (thermometry) maintaining control of the applied power. The aforementioned connect and disconnect function is accomplished by the switch 24. As also indicated previously, while the apparatus 20 functions as an N-way combiner during the receive mode of operation it now becomes an N-way divider during the transmit mode of operation. The transmit/receive switch 24 may be provided in several different embodiments including a mechanical and an electronic embodiment. If the switch 24 is an electronic switch such as through the use of ferrite duplexing and/or switching, insertion loss becomes a critical factor. A mechanical switch has isolation greater than 60 dB with an insertion loss of less than 0.1 dB. The switching time is slow with the mechanical switch, however, switching speed is not that critical in this particular application.

Reference is now made to FIG. 2 which shows an alternate embodiment of the present invention. The approach use in FIG. 2 employs a duplexer to separate the transmit and receive functions, basically allowing the insertion signal into each of the separate paths or channels. This particular approach allows independent control of the power level applied to each channel, assuming the phase coherency of the individual transmitter paths can be maintained.

In FIG. 2 the same reference characters have been used to identify similar components to those illustrated if FIG. 1. Thus there is provided a plurality of antennae. These antennae couple to a plurality of reflectometers which in turn couple to a plurality of phase shifters 16. The phase shifters in turn connect to a plurality of circulators 30. These circulators also couple to the multi-input N-way power combiner 32. FIG. 2 also shows the N-way power divider 34. The input to this divider is from the microwave transmitter. The several outputs of the power divider couple to the separate channels and thus there are preferably the same number of outputs from the divider 34 as there are antennae. Each of these outputs couple by way of a power amplifier 36 and single pole/single throw switch 38 to the third terminal of the circulator 30. With regard to the combiner 32 it is noted that it also has an equal number of input terminals to antennae. The output of the combiner 32 couples by way of the single pole/single throw switch 42 to the radiometer.

In the embodiment of FIG. 2, during the receive mode of operation the N-way power combiner 32 is operational but the N-way power divider 34 is non-operational. The microwave transmitter is not operating but the microwave radiometer is ready for operation and ready for the adjustment of the phase shifters. Thus, during the receive mode of operation the tumor itself functions as the signal generator and signals are coupled of each of the separate channels by way of the antenna, reflectometer and phase shifter of each channel to the circulator 30. The single pole/single throw switch 38 is open and thus the signal path is from the circulator 30 directly into the N-way power combiner 32. The single pole/single throw switch 42 is closed and thus the combined signal at the output of the combiner 32 couples to the radiometer. The individual phase shifters 16 are then separately adjusted to maximize the signal at the radiometer. This now establishes signal paths for optimum signal coupling and in particular optimizes the signal path characteristics in the signal path between the tumor and the antennae or in other words in the non-homogeneous tissue.

After the phase shifters have been adjusted and the radiometer signal is maximized, then the system switches to the transmit mode of operation. In this mode of operation the N-way power combiner 32 is essentially disabled and the transmitter sends the microwave signal to the N-way power divider 34 where the signal is divided and couples to each of the separate channels by way of the separate power amplifiers 36 and single pole/single throw switches 38. The single pole/single throw switches 38 are closed so that the signals couple to the circulator 30 and from there by way of the phase shifters, reflectometers and antennae to the tumor site. The phase shifters 16 having been previously adjusted and set at the optimum conditions for transmission, provide for an optimization of the signal coupled to the tumor site achieving a beam forming of this signal so that optimum heating occurs at the tumor site.

The radiometer itself generates noise that contributes to the overall noise of the system. Therefore, the total system output contains not only noise received by the antennae but noise generated within the system. The power levels associated with the transmitter cause a thermal elevation of the components and transmission common to the receive path. This, in turn produces phase and amplitude changes thus requiring frequency adjustment utilizing the radiometer during the receive mode of operation when the transmitter power is off. This adjustment may be minimized by maintaining simplicity and common componentry in each part. Antennae mismatch can be taken into account through the use of a reflectometer as illustrated in both embodiments during the transmit mode of operation. This allows the measurement of forward and reflected power. The preferred loose-coupling associated with the reflectometer has negligible impact on signal loss.

The technique of the present invention can be used with both invasive and non-invasive antennae elements. It should further be noted that the radiometer need not be at the same frequency as the transmitter. Frequency separation can be used along with the use of filtering, if needed, to provide further isolation of the sensitive receiver from the transmitter.

Figure 3:
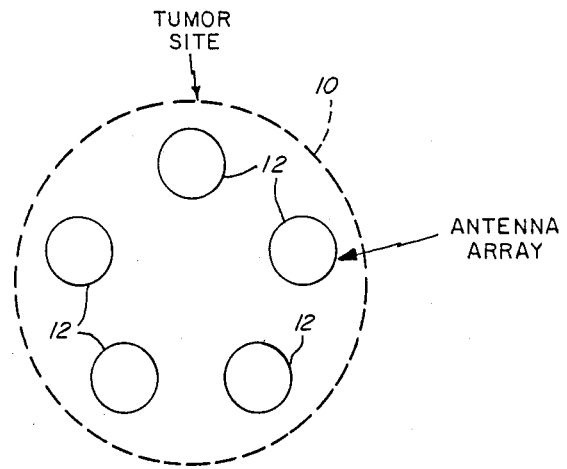
FIG. 3 schematically illustrates an antenna cluster as may be employed in accordance with the invention.

Reference is also made herein to FIG. 3 which shows one embodiment of an antenna cluster. This happens to show an embodiment in which there are five antennae employed. FIG. 3 also shows these antennae as they relate to the tumor site 10.

As indicated previously, once the tumor has been located by other techniques and the size thereof determined then different forms of antenna array may be employed.

Having now described a limited number of embodiments of the present invention it should now be apparent to those skilled in the art that numerous other embodiments and modifications thereof may be contemplated as falling within the scope of the present invention as defined by the appended claims.

What is claimed is:

1. A system for hyperthermia treatment of a cancerous tumor, comprising;
an antenna array including a plurality of antennae adapted to be disposed over the tumor site,
means for combining the signals from the antennae to provide a combined signal and including means for separately adjusting the phase of each of the antennae signals to maximize said combined signal,
transmitter means for generating a microwave signal,
and means for dividing the transmitter means signal for coupling via said means for separately adjusting the phase, after adjustment thereof, to said plurality of antennae, respectively.

2. A system as set forth in claim 1 wherein said means for combining includes an N-way combiner.

3. A system as set forth in claim 2 wherein said means for separately adjusting includes separate phase shifters coupled between the N-way combiner and antenna array.

4. A system as set forth in claim 3 including means for switching between transmit and receive modes.

5. A system as set forth in claim 3 wherein said means for dividing includes an N-way divider.

6. A system as set forth in claim 5 including a plurality of circulators each coupling between the N-way combiner and respective phase shifter.

7. A system as set forth in claim 6 including means coupling the transmitter means to the divider and means coupling the output of the divider to the circulators.

8. A system as set forth in claim 7 including a radiometer coupled from said N-way combiner and for receiving said combined signal therefrom.

9. A system as set forth in claim 8 wherein said means coupling the divider to the circulators includes an amplifier and switch coupled in series.

10. A method of hyperthermia treatment of a cancerous tumor comprising the steps of, providing an antenna array of a plurality of antennae disposed over the tumor site and each having a separate signal, combining the separate signals from the antennae to provide a combined signal representative of tumor site temperature, adjusting the phase of the separate antennae signals so as to maximize said combined signal and maintaining the thus-adjusted signals, providing a transmitter of electromagnetic energy, and coupling the transmitter output separately to each antenna while maintaining the previously set phase to provide beam focusing of the electromagnetic energy onto the tumor site.

11. A method as set forth in claim 10 wherein said transmitter provides a transmitter signal, and wherein the step of coupling the transmitter output to each antenna includes dividing the transmitter signal.

12. In a system including a microwave radiometric detector operable during a receive mode of operation to establish signal path characteristics, and a microwave transmitter operable during a transmit mode of operation to provide a microwave transmitter signal, a method of hyperthermia treatment of a cancerous tumor, comprising the steps of, providing an antenna array of a plurality of antennae disposed over the tumor site, providing separate bi-directional signal channels each coupled to an antenna and each having a separate channel signal, combining the separate channel signals for coupling to said microwave radiometric detector during the receive mode of operation, adjusting the phase of the separate antenna signals so as to maximize the signal detected at the microwave radiometric detector, and dividing the microwave transmitter signal for coupling to said signal channels during the transmit mode of operation to provide beam focusing of the microwave energy onto the tumor site.

* * * * *